(12) United States Patent
Skinner et al.

(10) Patent No.: US 9,297,814 B2
(45) Date of Patent: Mar. 29, 2016

(54) METHODS OF DETECTING OVARIAN CANCER

(71) Applicants: WISCONSIN ALUMNI RESEARCH FOUNDATION, Madison, WI (US); WAKE FOREST UNIVERSITY HEALTH SCIENCES, Winston-Salem, NC (US)

(72) Inventors: Halcyon Gerald Skinner, Middleton, WI (US); Gary G. Schwartz, Winston-Salem, NC (US)

(73) Assignees: WISCONSIN ALUMNI RESEARCH FOUDATION, Madison, WI (US); WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 81 days.

(21) Appl. No.: 14/147,941

(22) Filed: Jan. 6, 2014

(65) Prior Publication Data
US 2014/0193919 A1    Jul. 10, 2014

Related U.S. Application Data

(60) Provisional application No. 61/748,969, filed on Jan. 4, 2013.

(51) Int. Cl.
*G01N 33/84*    (2006.01)
*G01N 33/48*    (2006.01)
*G01N 33/574*   (2006.01)

(52) U.S. Cl.
CPC .......... *G01N 33/84* (2013.01); *G01N 33/57449* (2013.01); *G01N 2333/765* (2013.01)

(58) Field of Classification Search
CPC .......... G01N 2800/36; G01N 2800/50; G01N 2800/60; G01N 33/48; G01N 33/49; G01N 33/492; G01N 33/74; G01N 33/78; G01N 33/92; G01N 33/68; G01N 33/6812; G01N 33/84; G01N 33/57449; G01N 2333/765
USPC ............ 436/63, 64, 74, 79, 88, 71, 86; 435/4, 435/29
See application file for complete search history.

(56) References Cited

U.S. PATENT DOCUMENTS

| | | | |
|---|---|---|---|
| 7,279,294 B2 * | 10/2007 | Morin et al. | 435/7.23 |
| 2009/0098595 A1 * | 4/2009 | Chow | 435/29 |
| 2010/0167325 A1 | 7/2010 | Schwartz et al. | |

OTHER PUBLICATIONS

Schwartz et al. Gynecologic Oncology, vol. 129, Jan. 9, 2013, pp. 169-172.*
Abraham, Jame; "OVA1 Test for Preoperative Assessment of Ovarian Cancer"; Community Oncology; 7(6); pp. 249-251; (2010).
Skinner, Halcyon G. and Schwartz, Gary G.; "A Prospective Study of Total and Ionized Serum Calcium and Fatal Prostate Cancer"; Cancer Epidemiol Biomarkers Prev; 18(2); pp. 575-578; (2009).
Skinner, Halcyon G. and Schwartz, Gary G.; "Serium Calcium and Incident and Fatal Prostate Cancer in the National Health and Nutrition Examination Survey"; Cancer Epidemiol Biomarkers Prev 17(9); pp. 2302-2305; (2008).
Suwaki et al.; "Parathyroid Hormone-related Protein as a Potential Tumor Marker: A Case Report of Ovarian Clear Cell Carcinoma"; J. Obstet. Gynaecol. Res.; 32(1); pp. 94-98; (2006).
Toriola et al.; "Independent and Joint Effects of Serum 25-hydroxyvitamin D and Calcium on Ovarian Cancer Risk: A Prospective Nested Case-Control Study"; European Journal of Cancer; 46; pp. 2799-2805; (2010).
Ueland, et al.; "Effectiveness of a Multivariate Index Assay in the Preoperative Assessment of Ovarian Tumors"; Obstetrics & Gynecology; 117(6); pp. 1289-1297; (2011).
Arnold, Greg, abstractor; "Study Finds Calcium and Vitamin D Blood Levels Linked to Ovarian Cancer"; news article describing the results of Toriola; http://www.naturalhealthresearch.org/study-finds-calcium-and-vitamin-d-blood-levels-lin . . . ; 2 pages, posted Aug. 18, 2010, printed Oct. 21, 2015.
Brown, Edward M.; "Calcium-Sensing Receptor" from Vitamin D, Second Edition, David Feldman (ed.), Elsevier Academic Press, MA, Chapter 31, pp. 551-562; (2005).
Dagdelen et al.; "Humoral Hypercalcemia of Beniganancy Secondary to Parathyroid Hormone-Related Protein Secreting Uterine Leiomyoma"; Am. J. Med. Sci., 335(5); pp. 407-408; (2008).
Goltzman and Kremer; "Target Genes: PTHrP" from Vitamin D, Second Edition, vol. 1, David Feldman Ed., Elsevier Academic Press, MA, pp. 737-749; (2005).
Goltzman, David; "Hypercalcemia"; from NCBI Bookshelf; http://www.ncbi.nlm.nih.gov/books/NBK2790371/ 8 pages, Endotext, last updated Apr. 12, 2015, printed Oct. 21, 2015.
Rahil and Kahn; "Humoral Hypercalcemic Crisis in a Pregnant Woman with Uterine Leiomyoma"; J. Emerg. Trauma Shock, 5(1), pp. 87-89; (2012); http://www.ncbi.nlm.nih.gov/pmc/articles/PMC3299164/?report=printable.
Ravakhah, Keyvan; "Humoral Hypercalcemia Associated with a Uterine Fibroid", Annals of Internal Medicine; 130(8), p. 702, (1999).
Weir et al.; "Relative Overexpression of the Parathyroid Hormone-Related Protein Gene in Human Leiomyomas"; Journal of Clinical Endocrinology and Metabolism; 78(3); pp. 784-789; (1994).

* cited by examiner

*Primary Examiner* — Maureen Wallenhorst
(74) *Attorney, Agent, or Firm* — Cantor Colburn LLP

(57) ABSTRACT

Methods of screening human female subject for a risk of ovarian cancer are described. High levels of calcium in serum are shown to be significantly positively associated with the risk of ovarian cancer and can advantageously be used to triage women into risk categories for more intensive testing. Also included are preoperative methods of determining if an adnexal mass is likely to be malignant or benign.

16 Claims, No Drawings

METHODS OF DETECTING OVARIAN CANCER

CROSS-REFERENCE TO RELATED APPLICATIONS

This application claims priority to U.S. Provisional Application Ser. No. 61/748,969 filed on Jan. 4, 2013, which is incorporated herein by reference in its entirety.

FIELD OF THE DISCLOSURE

The present disclosure is related to methods of detecting ovarian cancer using a novel serum biomarker.

BACKGROUND

Ovarian cancer is the most fatal of the gynecologic cancers. The high fatality rate results from the late stage of presentation, at which time ovarian cancers have metastasized and their curability is low. In theory, early diagnosis of ovarian cancer might be accomplished through the use of biomarkers in blood or urine. However, the most widely studied serum marker for ovarian cancer, CA-125, is elevated in only 50% of women with curable (Stage 1) disease. Consequently, there is great interest in the discovery of additional biomarkers and predictive methods that could help to detect ovarian cancers at a curable stage.

BRIEF SUMMARY

In an aspect, a preoperative method of determining the likelihood that an adnexal mass in a female subject is malignant or benign comprises providing a blood sample collected from the subject; determining a total serum calcium level and a serum albumin level in the blood sample; comparing the total serum calcium level and the serum albumin level of the blood sample to a predictive model that includes total serum calcium and serum albumin levels for a population; and determining that the adnexal mass is likely to be malignant when the total serum calcium level in the blood sample is high normocalcemic to hypercalcemic or deviates upward from normal based on the predictive model, or determining that the adnexal mass is likely to be benign when total serum calcium level in the blood sample is normocalcemic or lower, is normal based on the predictive model, or deviates downward from normal based on the predictive model.

In another aspect, a preoperative method of determining if an adnexal mass in a female subject is likely to be malignant or benign comprises providing a blood sample collected from the subject; determining a total serum calcium level and an albumin level in the blood sample, and calculating an albumin-corrected calcium level of the blood sample from the subject, or determining the ionized serum calcium level of the blood sample from the subject; comparing the albumin-corrected calcium level of the blood sample from the subject to a predictive model that includes albumin-corrected calcium levels for a population, or comparing the ionized serum calcium level of the blood sample from the subject to a predictive model that includes ionized serum calcium levels for a population; and determining that the adnexal mass is likely to be malignant when the albumin-corrected calcium level in the blood sample is high normocalcemic to hypercalcemic or deviates upward from normal based on the predictive model, determining that the adnexal mass is likely to be benign when the albumin-corrected calcium level in the blood sample is normocalcemic or lower, is normal based on the predictive model, or deviates downward from normal based on the predictive model, determining that the adnexal mass is likely to be malignant when the ionized serum calcium level in the blood sample is high normocalcemic to hypercalcemic or deviates upward from normal based on the predictive model, or determining that the adnexal mass is likely to be benign when the ionized serum calcium level in the blood sample is normocalcemic or lower, is normal based on the predictive model, or deviates downward from normal based on the predictive model.

In an aspect, a method of screening for an increased risk of ovarian cancer in a human female subject comprises providing a blood sample collected from the subject; determining a level of total or ionized serum calcium in the blood sample; and determining that the subject has an increased risk of ovarian cancer when the level of total or ionized serum calcium in the blood sample is in the upper tertile compared to a normal distribution, wherein the subject is experiencing one or more symptoms of ovarian cancer and/or wherein the subject has a family history of breast or ovarian cancer.

In yet another aspect, a method of screening for an increased risk of ovarian cancer in a human female subject comprises providing a first blood sample and a second blood sample collected from the subject, wherein the first and second blood samples are taken at a first time interval; determining a level of total or ionized serum calcium in the first and second blood samples; and determining that the subject has an increased risk of ovarian cancer when the level of total or ionized serum calcium in said second blood sample is increased compared to the first blood sample, and the increase in total or ionized serum calcium is not accompanied by an increase in serum parathyroid hormone, and/or is accompanied by a detectable level of parathyroid-hormone-related peptide.

The above-described and other features will be appreciated and understood by those skilled in the art from the following detailed description, drawings, and appended claims.

DETAILED DESCRIPTION

One approach to cancer biomarker discovery is to identify a factor(s) that is differentially expressed in individuals with and without cancer and to examine the ability of the factor to detect cancer in an independent sample of individuals with and without cancer. Some ovarian cancers are known to express increased levels of parathyroid hormone-related protein (PTRHrP), an oncofetal protein that is the principal agent of hypercalcemia of malignancy. PTHrP acts to increase the release of calcium from bone and to retard the excretion of calcium in the kidney, causing calcium levels in serum to rise. Although only a small minority of ovarian cancers are characterized by hypercalcemia (i.e., serum calcium levels>upper limit of the normal reference range), the evolution of hypercalcemia in ovarian cancer may be gradual. That is, tumors are likely evolve from normocalcemia to high normocalcemia before they cross the threshold to hypercalcemia. Thus, as shown herein, high serum calcium levels can predict ovarian cancer.

As used herein, the normal range for total serum calcium ("normocalcemia") depends upon the laboratory, but is typically 8.5-10.4 mg/dl. Levels below 8.5 mg/dl are "hypocalcemia "and levels >10.4 mg/dl are "hypercalcemia". Levels of approximately 9.8 mg/dl and above that are within the normal range, but are high normal, are "high normocalcemia". Values less than 9.8 mg/dl are generally considered to not be high normocalcemic.

In an embodiment, a preoperative method of determining if an adnexal mass in a female subject is likely to be malignant or likely to be benign comprises providing a blood sample collected from the subject; determining a total serum calcium level and a serum albumin level in the blood sample; comparing the total serum calcium level and the serum albumin level of the blood sample to a predictive model that includes total serum calcium and serum albumin levels for a population; and determining that the adnexal mass is likely to be malignant when the total serum calcium level in the blood sample is high normocalcemic to hypercalcemic or deviates upward from normal based on the predictive model, or determining that the adnexal mass is likely to be benign when total serum calcium level in the blood sample is normocalcemic or lower, is normal based on the predictive model, or deviates downward from normal based on the predictive model.

In another embodiment, a preoperative method of determining if an adnexal mass in a female subject is likely to be malignant or benign comprises providing a blood sample collected from the subject; determining a total serum calcium level and an albumin level in the blood sample, and calculating an albumin-corrected calcium level of the blood sample from the subject, or determining the ionized serum calcium level of the blood sample from the subject; comparing the albumin-corrected calcium level of the blood sample from the subject to a predictive model that includes albumin-corrected calcium levels for a population, or comparing the ionized serum calcium level of the blood sample from the subject to a predictive model that includes ionized serum calcium levels for a population; and determining that the adnexal mass is likely to be malignant when the albumin-corrected calcium level in the blood sample is high normocalcemic to hypercalcemic or deviates upward from normal based on the predictive model, determining that the adnexal mass is likely to be benign when the albumin-corrected calcium level in the blood sample is normocalcemic or lower, is normal based on the predictive model, or deviates downward from normal based on the predictive model, determining that the adnexal mass is likely to be malignant when the ionized serum calcium level in the blood sample is high normocalcemic to hypercalcemic or deviates upward from normal based on the predictive model, or determining that the adnexal mass is likely to be benign when the ionized serum calcium level in the blood sample is normocalcemic or lower, is normal based on the predictive model or deviates downward from normal based on the predictive model.

In other words, when the total, albumin-corrected or ionized serum calcium is in the range of high normocalcemia, or upward or high deviation from normal (toward high normocalcemia) based on a model population, the adnexal mass has an increased likelihood of being malignant. Conversely, when the total, albumin-corrected or ionized serum calcium is normocalcemic or lower (hypocalcemic, low normocalcemic, normocalcemic), or is normal or deviates downward from normal (toward low normocalcemia) based on a model population, the adnexal mass is more likely to be benign.

When the method includes determining ionized serum calcium, the method optionally further comprises determining serum albumin. The predictive model can include both ionized serum calcium and serum albumin levels for a population.

As used herein an adnexal mass is an abdominal mass in a female subject that may be cancer (malignant) or may be a benign (non-malignant) tumor such as a fibroid. The term "adnexa" refers to the ovary, fallopian tubes, uterus and related structures. When a female patient presents to a physician such as an obstetrician/gynecologist with an abdominal mass, the mass may be removed and the nature of the mass is determined after removal. Such masses can be removed by an obstetrician/gynecologist, a general surgeon, or a gynecologic oncologist. Benign masses can be routinely removed by an obstetrician/gynecologist or a general surgeon. In the case of malignant masses, the survival rate is greatly improved when the surgery is performed by a gynecologic oncologist. Thus, the preoperative distinction between adnexal masses that are likely to be malignant from adnexal masses that are likely to be benign masses is critical for appropriate surgical referral and treatment of the subject. If the likelihood of malignancy is ascertained with a high level of certainty, the obstetrician/gynecologist or general surgeon can decide which cases to keep and which cases to refer to a specialist such as a gynecological oncologist. As described herein, the measured serum calcium/albumin levels in the blood sample can be used to differentiate adnexal masses that are likely to be malignant from adnexal masses that are likely to be benign. Because the tests described herein have a high sensitivity (correctly identifies the malignant masses) and a high specificity (correctly identifies the non-malignant masses), the treatment outcome for the patient with a malignant mass can be improved by appropriate referral and treatment and the patient and physician relationship can be maintained if the generalist can identify the cases he/she can treat without referral to a specialist.

Serum calcium levels are commonly measured as total, ionized, or albumin-corrected calcium levels. Approximately half of total serum calcium is in the "free" or ionized state; approximately 40% is bound to serum proteins, principally albumin, and the remainder is bound to anions. Ionized serum calcium is the biologically active fraction of total serum calcium. While ionized serum calcium levels can be measured as disclosed herein, ionized serum calcium levels can also be estimated by adjusting total serum calcium levels by the albumin level. Levels of albumin-corrected serum calcium are calculated for women with a serum albumin below 4.0 g/dL using a standard formula (0.8 times the difference between 4.0 g/dL and the observed albumin level, plus the observed total serum calcium level in mg/dL). As shown herein, because both calcium and albumin levels provide information about the malignant/benign state of a mass, the albumin-corrected serum calcium level can provide valuable information.

In the first embodiment, the total serum calcium level and serum albumin level in the blood sample are measured and compared to a predictive model that includes total serum calcium and serum albumin levels for a population. As explained in Example 2, it was unexpectedly found that modeling calcium and albumin as separate variable provides additional predictive power compared to modeling calcium corrected for albumin. For example, modeling calcium and albumin as separate variables gives a larger area under the curve (AUC) than does modeling these variables as the single variable, albumin-adjusted serum calcium. In addition to serum calcium and serum albumin, the predictive model may include additional covariates such as age, body mass index, menopausal status, parity, or a combination thereof As used herein, parity means the condition of women with respect to having children. Women who have not born children are nulliparous, those that have one child are primiparous, and multiple births make a woman multiparous. Parity is relevant because nulliparity is an established risk factor for ovarian cancer (in some cases it may be a symptom of ovaries that are not completely functional), and parity confers some protection. The method includes determining that the adnexal mass is likely to be malignant when the total serum calcium level in the blood sample deviates from normal based on the predictive model, or determining that the adnexal mass is benign when total serum calcium level in the blood sample is normal based on the predictive model. For example, in the study of 514 women presented herein, the risk of malignancy increased 10-fold in a woman whose albumin-adjusted serum calcium was 10 mg/dl or higher, which is high normocalcemia.

In the second embodiment, the total serum calcium level and albumin level in the blood sample are measured and an albumin-corrected calcium level is calculated. The albumin-corrected calcium level for the sample is compared to a predictive model that includes albumin-corrected calcium levels for a population. Alternatively, the ionized serum calcium is measured and compared to a predictive model that includes ionized serum calcium levels for a population. In this embodiment, the method may further comprise determining serum albumin levels which may be incorporated into the predictive model. The predictive model may include additional covariates such as age, body mass index, menopausal status, parity, or a combination thereof The method includes determining that the adnexal mass is likely to be malignant when the albumin-corrected calcium level in the blood sample is high normocalcemic to hypercalcemic or deviates upward from normal based on the predictive model, or determining that the adnexal mass is benign when the albumin-corrected calcium level in the blood sample is not high normocalcemic, is normal based on the predictive model, or deviates downward from normal based on the predictive model. In one embodiment, the elevated albumin-corrected calcium level is greater than or equal to 9.8 mg/dl When it is determined that the adnexal mass is likely to be malignant, the method may further comprise referring the subject to a gynecological surgeon for removal of the malignant adnexal ovarian mass.

In one embodiment, a method of screening for an increased risk of ovarian cancer in a human female subject comprises providing a blood sample collected from the subject; determining a level of total or ionized serum calcium in the blood sample; and determining that the subject has an increased risk of ovarian cancer when the level of total or ionized serum calcium in the blood sample is increased compared to a normal distribution, for example, the level of total or ionized serum calcium in the blood sample is in the upper tertile compared to a normal distribution.

In one embodiment, the increase in total or ionized serum calcium is not accompanied by an increase in serum parathyroid hormone, and/or is accompanied by a detectable level of parathyroid-hormone-related peptide. Normal (intact) serum parathyroid hormone levels are 10-65 mg/ml for an individual greater than 17 years of age, thus increased levels are greater than this value.

In one embodiment, determining that the subject has an increased risk of ovarian cancer further comprises calculating an ovarian cancer risk score for the subject that is a predicted probability of ovarian cancer that is calculated from several input variables. In addition to serum calcium levels, the risk score can take into account familial history, history of other cancer diagnoses, age, other biological markers and other risk factors. The input values may be scaled and subject to mathematical transformation and then combined using an algorithm that incorporates the several variables in a non-linear fashion to output the predicted probability of ovarian cancer.

Subjects are human females of any age. In one embodiment, the human female subject is suspected of having ovarian cancer, for example, the human female subject is experiencing one or more symptoms of ovarian cancer. For example, the subject may be experiencing abdominal pressure, swelling or bloating; pelvic pain or discomfort; nausea; constipation; urinary problems such as frequent urination or urgent need to urinate; loss of appetite or a quick feeling of fullness; increased abdominal circumference or tight-fitting clothing; persistent lack of energy, low back pain; or other symptoms. Often these symptoms start suddenly, persist daily and do not go away. One of the difficulties with diagnosing ovarian cancer is that many of the signs and symptoms are nonspecific and mimic other disorders such as digestive disorders. In one embodiment, the human female subject has a family history of ovarian or breast cancer.

In a still further embodiment, the human female subject has had therapy for ovarian cancer (e.g., surgery, radiation, chemotherapy). Thus, monitoring serum calcium in such a subject can be used to detect disease recurrence.

Blood samples are collected from subjects by a suitable means, including but not limited to finger stick, venipuncture/phlebotomy, and the like. In one embodiment, the blood sample is whole blood as it is withdrawn or collected from the subject, which is then at least partially purified (e.g., to produce blood plasma) to produce the blood sample on which the detecting step is carried out.

The detecting step or procedure is carried out in accordance with known techniques for detecting/quantifying serum calcium, or variations thereof that will be apparent to those skilled in the art. In general, the detecting step is a quantitative detecting step. Exemplary detecting procedures include, but are not limited to, absorption spectrometry (e.g., infrared absorption spectrometry, atomic absorption spectrometry), detection with an ion- (specifically calcium) selective electrode, colorimetric detection, fluorescent detection, enzymatic detection, and the like.

Ionized serum calcium can be detected with an ion-selective electrode in accordance with known techniques, or variations thereof that will be apparent to those skilled in the art. In general, such methods involve contacting the sample with an ion-selective electrode; and then measuring (e.g., potentiometrically) ionized calcium in the sample through the electrode. Thus in one embodiment, the serum calcium is ionized serum calcium, and wherein said detecting step is carried out by contacting said sample with an ion-selective electrode; and potentiometrically measuring ionized calcium in said sample through said electrode.

In one embodiment, said serum calcium is total serum calcium and detecting is carried out by absorption spectrometry.

In another embodiment, said serum calcium is total serum calcium, and the detecting step is carried out by atomizing said sample in an atomic absorption spectrophotometer to provide an atomized sample; illuminating said atomized sample with light in said atomic absorption spectrophotometer; detecting light from said atomized sample with a detector; and determining the amount of total serum calcium in said sample from said detected light by atomic absorption spectrophotometry.

In one embodiment, atomic absorption spectrophotometry is, in general, carried out by atomizing (e.g., by a flame or heat) the sample in an atomic absorption spectrophotometer to provide an atomized sample; then illuminating the atomized sample with light (e.g., laser light) in the spectrophotometer; then detecting light from said atomized sample with a detector; and then determining the amount of total serum calcium in said sample from said detected light by atomic absorption spectrophotometry. Samples may be diluted with lanthanum HCl to reduce viscosity and interference, and strontium may be added or included as an internal standard to correct for fluctuations in the flame and atomization rate.

Total serum calcium can be colorimetrically analyzed by, for example, combining the sample with a metallochromic indicator dye that binds calcium to form a complex (e.g., arsenazo dye or orthocresolphthalein complexone); and then colorimetrically measuring the formation of the complex (e.g., with a colorimeter or spectrophotometer) to determine the amount of calcium in said sample.

Total serum calcium can be fluorescently analyzed by, for example, combining said sample with a chelating agent (e.g., EDTA, EGTA) that binds calcium and forms a fluorescent complex therewith; and then detecting fluorescence from said sample to determine the amount of calcium in said sample.

Total serum calcium can be enzymatically determined by, for example, combining the sample with an enzyme that is either activated or inhibited by calcium, and then detecting the activation or inhibition of said enzyme to determine the amount of calcium in said sample. Exemplary enzymes include, but are not limited to, alpha amylase, phospholipase D, and urea amidolyase.

As shown herein, a woman with a total serum calcium in the upper tertile of the normal distribution is approximately three times more likely to be diagnosed with ovarian cancer; a woman with an ionized serum calcium in the upper tertile of the normal distribution is greater than three times more likely to be diagnosed with ovarian cancer.

As used herein, the term "normal distribution" means the distribution of total and/or ionized serum calcium levels for a normal population, that is, a population not characterized as at an increased risk of ovarian cancer. In one embodiment, said subject has an increased risk of ovarian cancer when the level of total or ionized serum calcium in said sample is in the middle or upper tertile compared to a normal distribution. In another embodiment, said subject has an increased risk of ovarian cancer when the level of total or ionized serum calcium in said sample is in the middle or upper tertile compared to a normal distribution.

In a further embodiment, when the level determined is the level of total serum calcium, the level of total serum calcium may be increased by 0.1 mmol/L (0.25 mg/dl) or more compared to a midpoint of normal distribution.

In a yet further embodiment, when the level determined is the level of ionized serum calcium, the level of ionized serum calcium may be increased by 0.1 mmol/L (0.25 mg/dl) or more compared to a midpoint of a normal distribution.

In addition, by using the simple procedure of serum calcium screening, women can be stratified into risk categories years before ovarian cancer occurs or would otherwise be detected. Women in the highest risk group may opt to have more intensive screening, or to begin screening at an earlier age.

In one embodiment, when the woman is found to be at risk of having ovarian cancer, such as when said sample is in the middle or upper tertile compared to a normal distribution, further testing may be warranted. Thus, serum calcium, specifically serum ionized calcium, can be used to triage women into risk categories, with women at highest risk (e.g., upper tertile) offered more intensive testing such as CA-125 screening and/or ultrasonography and/or continued monitoring of ionized serum calcium (i.e., in order to detect further increases).

CA-125 (cancer antigen 125) is a serum marker for ovarian cancer. Although CA-125 levels are elevated in >90% of women with advanced stage ovarian cancer, they are elevated in only 50% of women with stage I disease. CA-125 screening is often done in conjunction with ultrasound. Because of the expense of using these methods and the inability to detect ovarian cancer in women with early stage disease, along with the very high numbers of "false positive tests" which subject women without cancer to unnecessary surgery, these methods are not suitable for population screening. However, pre-screening for elevated serum total or ionized calcium can allow the selection of the highest risk women for further testing for CA-125 and/or ultrasound.

In another embodiment, the serum calcium test may improve on the recently FDA-approved OVA-1 test which is used to help determine whether on ovarian mass should be resected by an ob/gyn oncologist (when the test is positive), or whether it can be resected by a gynecologist (when it is negative). OVA-1 is a test that combined five biomarkers, specifically beta-2 microglobulin, CA 125-II, apolipoprotein Al, prealbumin, and transferrin. Thus, in one embodiment, a woman with an ovarian mass which may or may not be malignant is, based on her serum calcium levels is further subjected to blood testing for beta-2 microglobulin, CA 125-II, apolipoprotein Al, prealbumin, and transferrin. In another embodiment, a test subject such as a woman at risk for ovarian cancer has tested positive in the OVA1 test and is further subjected to testing using serum calcium levels as disclosed herein.

In another embodiment, when the subject is found to be at risk of ovarian cancer, the method further comprises assaying a blood sample for human epididymis protein 4. Human epididymis protein 4 (HE4) is a marker for the recurrence of progressive disease in patients with epithelial ovarian cancer. Testing HE4 is generally used in conjunction with other clinical methods for monitoring ovarian cancer.

In another embodiment, a method of screening for an increased risk of ovarian cancer in a human female subject comprises providing a first blood sample and a second blood sample collected from the subject, wherein the first and second blood sample are taken at a time interval t; determining a level of total or ionized serum calcium in the first and second blood samples; and determining that the subject has an increased risk of ovarian cancer when the level of total or ionized serum calcium in the second blood sample is increased compared to the first blood sample, and the increase in serum calcium is not accompanied by an increase in serum parathyroid hormone, and/or is accompanied by a detectable level of parathyroid-hormone-related peptide. In one aspect, an increase in total or ionized serum calcium is an increase of 10% or more. In specific embodiments, the time interval is 1 week, 2 weeks, 3 weeks, 4 weeks, 5 weeks, 6 weeks, 6 months, 1 year or longer.

Serum calcium levels are generally very stable in health and a given level, particularly of ionized calcium, is characteristic of any individual (e.g., it usually does not vary by more than 1%). Thus, if a woman has serial measurements of ionized calcium over time and these are progressively increasing, this may increase suspicion of an occult ovarian tumor. While a rising ionized calcium is also characteristic of primary hyperparathyroidism, in the case of primary hyperparathyroidism, typically the serum calcium and the serum parathyroid hormone (PTH) will both be high. Conversely, in ovarian cancer that is accompanied by high normocalcemia, the serum level of PTH is expected be low, as it is suppressed by the high serum calcium, and the elevation is serum calcium is caused by factors other than high PTH (notably, but not exclusively, high PTH-related peptide (PTHrP). Thus, a gradually increasing serum calcium, specifically one accompanied by a low PTH or a detectable PTHrP, may be biomarkers of an occult ovarian malignancy.

The invention is further illustrated by the following non-limiting examples.

EXAMPLE 1

Identifying a Risk Factor for Ovarian Cancer by Associating Health Histories and Serum Calcium Levels in Two Nationally-Representative Prospective Cohorts Methods The hypothesis that high normocalcemia can be used to identify women at increased risk for ovarian cancer was tested using data on serum calcium in two nationally-representative prospective cohorts, the Third National Health and Nutrition Examination Surveys (NHANES III) and the NHANES Epidemiologic Follow-up Study (NHEFS).

Baseline data and serum samples were collected as part of NHANES III between 1988 and 1994. Total and ionized serum calcium levels were measured using ion-specific electrodes and were pH-adjusted as is known in the art. Because the protein binding of calcium is affected by pH, ionized calcium in blood is commonly corrected to standard pH. Approximately half of total serum calcium is in the "free" or ionized state; approximately 40% is bound to serum proteins, principally albumin, and the remainder is bound to anions. Ionized serum calcium is the biologically active fraction of total serum calcium. Because the measurement of ionized calcium is technically more challenging and more expensive than the measurement of total serum calcium, ionized calcium levels often are estimated by calculating serum calcium levels adjusted for serum albumin. Levels of albumin-adjusted serum calcium were calculated for women with a serum albumin below 4.0 g/dL using a standard formula (0.8 times the difference between 4.0 g/dL and the observed albumin, plus the observed total serum calcium in mg/dL).

The outcome in NHANES III was death attributed to ovarian cancer on the death certificate with mortality linkage through Dec. 31, 2006. Follow-up time was computed as the number of months between the baseline exam and death from ovarian cancer (events) or any other cause (censored), or Dec. 31, 2006 if participants were alive. Women who reported that they had no ovaries at baseline were excluded, but women with a prior personal history of non-ovarian cancers were included because they remain at risk for ovarian cancer. No follow-up for incident cases was performed for NHANES III and information about sub-types of ovarian cancer was not available.

A second, confirmatory, nationally-representative prospective study was conducted using the first NHANES Epidemiologic Follow-up Study (NHEFS) with incident ovarian cancer as the outcome. Women ages 25 to 75 years at baseline examination in 1971 to 1975 were included. Follow-up questionnaires for incident medical conditions were administered in 1982, 1986, 1987, and 1992. Women who reported having no ovaries at baseline were excluded, but women with a prior personal history of non-ovarian cancers were included, as in NHANES III. Follow-up time was computed as the interval between baseline examination and date of diagnosis with ovarian cancer (events), or a report of removal of both ovaries (censored), or the end of follow-up in December 1992. Data on ionized calcium were not available in NHEFS.

Cox proportional hazards regression models accounting for survey weights and the complex sampling design were used to estimate relative hazards and 95% confidence intervals for ovarian cancer death by incremental (0.1 mmol/L) differences in total serum calcium, albumin-adjusted serum calcium, and ionized serum calcium. Potential confounding by age, height, body mass index (BMI), race/ethnicity (black versus all other), cigarette smoking status (ever vs. never), nulliparity (no live births versus any), and use of oral contraceptives (ever vs. never) were computed. Statistical analyses were performed using R v 2.15.0 with the "survival" package as is known in the art.

Results

Table 1 shows selected characteristics of women in NHANES/NHEFS and NHANES III by categories of serum total calcium at baseline.

TABLE 1

Selected characteristics of women in the First National Health and Nutrition Examination Survey (NHANES), NHANES Epidemiology Follow-up Study (NHEFS) and Third National Health and Nutrition Examination Survey (NHANES III) by tertile of serum total calcium concentration at baseline.

|  | Baseline Total Serum Calcium Tertile in NHANES/NHEFS | | |
|---|---|---|---|
| Total Calcium Range (mmol/L) | 1.98-2.38 | 2.38-2.45 | 2.45-2.93 |
| Number of participants | 725 | 507 | 516 |
| Weighted Population | 19,842,226 | 13,751,362 | 13,913,528 |
| Ovarian cancer cases through 1992 | 1 | 1 | 6 |
| Person-months of follow-up | 158,280 | 106,800 | 107,988 |
| Mean total calcium (mmol/L) | 9.27 (0.08) | 9.69 (0.02) | 10.13 (0.08) |
| Mean age (years) | 45.80 (16.81) | 46.50 (17.77) | 47.75 (19.01) |
| Mean body mass index (kg/m$^2$) | 25.17 (6.40) | 25.45 (6.10) | 25.42 (6.19) |
| Mean albumin (g/dL) | 4.20 (0.39) | 4.35 (0.32) | 4.46 (0.31) |
|  | Baseline Total Serum Calcium Tertile in NHANES III | | |
| Total Calcium Range (mmol/L) | 1.57-2.26 | 2.26-2.34 | 2.34-3.29 |
| Number of participants | 2,644 | 2,219 | 2,127 |
| Weighted Population | 28,375,219 | 24,631,015 | 21,193,034 |
| Ovarian cancer deaths through 2006 | 3 | 4 | 4 |
| Person-months of follow-up | 442,665 | 262,210 | 341,803 |
| Mean total calcium (mmol/L) | 2.20 (0.08) | 2.31 (0.02) | 2.43 (0.08) |
| Mean ionized calcium (mmol/L) | 1.21 (0.04) | 1.24 (0.03) | 1.27 (0.05) |
| Mean age (years) | 42.53 (16.81) | 42.76 (17.77) | 44.74 (19.01) |

TABLE 1-continued

Selected characteristics of women in the First National Health and Nutrition Examination Survey (NHANES), NHANES Epidemiology Follow-up Study (NHEFS) and Third National Health and Nutrition Examination Survey (NHANES III) by tertile of serum total calcium concentration at baseline.

| | | | |
|---|---|---|---|
| Mean body mass index (kg/m$^2$) | 26.25 (6.40) | 26.20 (6.10) | 26.40 (6.19) |
| Mean albumin (g/dL) | 3.97 (0.39) | 4.11 (0.32) | 4.22 (0.31) |

Means and standard deviations account for the complex sampling design and survey weights in NHANES/NHEFS and NHANES III. Where means are given, standard deviations appear in parentheses.

Eleven ovarian cancer deaths were observed over 95,556 person-years of follow-up through Dec. 31, 2006, representing 137,404 ovarian cancer deaths in the United States. The range in total serum calcium in cases was 2.14 to 2.44 mmol/L and for ionized serum calcium was 1.17 to 1.31 mmol/L. The normal reference range for total serum calcium is approximately 2.17 to 2.52 mmol/L [8.7 to 10.1 mg/dL] and 1.12 to 1.32 mmol/L [4.5 to 5.3 mg/dL] for ionized serum calcium. The range of times from calcium measurement to death was 28 to 208 months. In multivariable Cox models, the relative hazard for fatal ovarian cancer was 1.52 per 0.1 mmol/L increase in total serum calcium (95% CI 1.06-2.19) and 2.44 per 0.1 mmol/L increase in ionized serum calcium (95% C.I. 1.45-4.09). Adjustment for race, cigarette smoking, height and BMI did not materially alter the estimates versus age-adjusted estimates. Further adjustment for nulliparity and the never use of oral contraceptives yielded relative hazards (RHs) of 1.46 (1.02-2.09) and 2.11 (1.16-3.83) for total and ionized serum calcium, respectively. Due to the small number of events, interactions between serum calcium concentration and covariates could not be explored.

TABLE 2

Multivariable adjusted relative hazards for ovarian cancer mortality by ionized, total, and albumin-adjusted serum calcium concentrations at baseline in the Third National Health and Nutrition Examination Survey (NHANES III).

| | Relative Hazard | 95% Confidence Interval |
|---|---|---|
| Ionized Calcium (per 0.1 mmol/L) | | |
| Age adjusted | 1.97 | (1.27, 3.04) |
| Age and covariates adjusted* | 2.44 | (1.45, 4.09) |
| Nulliparity and oral contraceptive adjusted† | 2.11 | (1.16, 3.83) |
| Total Calcium (per 0.1 mmol/L) | | |
| Age adjusted | 1.33 | (0.92, 1.92) |
| Age and covariates adjusted* | 1.52 | (1.06, 2.19) |
| Nulliparity and oral contraceptive adjusted† | 1.46 | (1.02, 2.09) |
| Albumin-Adjusted Calcium (per 0.1 mmol/L) | | |
| Age adjusted | 1.30 | (0.87, 1.93) |
| Age and covariates adjusted* | 1.47 | (1.02, 2.13) |
| Nulliparity and oral contraceptive adjusted† | 1.38 | (0.98, 1.96) |

All models account for complex sampling design and survey weights in NHANES III.
*Adjusted for age, body mass index, height, race (black versus all other), cigarette smoking status (ever/never).
†Adjusted for age, body mass index, cigarette smoking status (ever/never), nulliparity (yes/no), and oral contraceptive use (ever/never).

A second prospective population-based cohort, the NHEFS, was used to confirm these findings. There were 8 incident ovarian cancer cases in the NHEFS over 31,089 person-years of follow-up. The range of total serum calcium was 1.98 to 2.93 mmol/L. The range of times from calcium measurement to diagnosis with ovarian cancer was 12 to 240 months. The multivariable adjusted relative hazard for ovarian cancer for each 0.1 mmol/L increase in total serum calcium was 1.63 (95% CI 1.14-2.34). Adjusting for BMI, height, and cigarette smoking status did not materially change the association compared to adjusting for age alone. Further adjustment for nulliparity and ever use of oral contraceptives moderately strengthened the association with a RH of 1.75 (95% CI 1.27-2.42). Similar RHs were observed for 0.1 mmol/L increments of albumin-adjusted serum calcium.

TABLE 3

Multivariable adjusted relative hazards for ovarian cancer incidence by total and albumin-adjusted serum calcium concentrations at baseline in the National Health and Nutrition Examination Survey Survey Epidemiological Follow-up Study (NHEFS).

| | Relative Hazard | 95% Confidence Interval |
|---|---|---|
| Total Calcium (per 0.1 mmol/L) | | |
| Age adjusted | 1.66 | (1.16, 2.37) |
| Age and covariates adjusted* | 1.63 | (1.14, 2.34) |
| Nulliparity and oral contraceptive adjusted† | 1.75 | (1.27, 2.42) |
| Albumin-Adjusted Calcium (per 0.1 mmol/L) | | |
| Age adjusted | 1.68 | (1.16, 2.43) |
| Age and covariates adjusted* | 1.66 | (1.15, 2.40) |
| Nulliparity and oral contraceptive adjusted† | 1.78 | (1.28, 2.49) |

All models account for complex sampling design and survey weights in NHANES.
*Adjusted for age, body mass index, height, cigarette smoking status (ever/never).
†Adjusted for age, body mass index, cigarette smoking status(ever/never), nulliparity (yes/no), and oral contraceptive use (ever/never).

Discussion

In these nationally representative population-based cohorts, positive associations between total and ionized serum calcium levels and risk of ovarian cancer were observed. These associations remained significant after adjustment for known risk factors for ovarian cancer, including height and BMI and, for ionized serum calcium, remained so after further adjustment for nulliparity and the non-use of oral contraceptives.

These results from two population-based cohorts differ from those from a case-control study of total serum calcium and incident ovarian cancer reported previously in Torioloa et al. (Toriola A T, Surcel H-M, Calypse A, Grankvist K, Luostarinen T, Lukanova A, Pukkala E, Lehtinen M. Independent and joint effects of serum 25-hydroxyvitamin D and calcium on ovarian cancer risk: a prospective nested case-control study. Eur J Cancer 2010;46:2799-805). These authors studied 172 pregnant cases and 172 pregnant controls nested within the Finnish Maternity Cohort. They reported a significant inverse association between serum calcium and ovarian cancer that resulted from comparing cases and controls in the highest and lowest quartiles of total serum calcium (OR=0.41 95% CI 0.19-0.85). An inverse association was not apparent in the other quartiles [adjusted ORs and 95% CIs=1.0 (reference); 1.04 (0.55-1.96) and 0.84 (0.44-1.61)] and appears to result from the use of a control group with hypercalcemia. The upper limit of the normal range for serum calcium according to the assay used by Toriola et al. is 2.55 mmol/L (10.2 mg/dL). Of their 172 controls, 44 (26%) had serum calcium levels beyond the normal range, including 17 (10%) with serum values≥2.8 mmol/L (11.2 mg/dL).

It was considered how the results presented herein could be influenced by chance and by confounding. Although the number of events in each cohort was small, the confidence intervals around the relative hazards excluded the null value and indicated strong or very strong evidence for the observed associations. It is possible that a high proportion of ovarian cancers of a hypercalcemic type were observed by chance. Data on the type of ovarian cancer were not available in these cohorts. However, the type of ovarian cancer most often associated with hypercalcemia, small cell carcinoma, is rare and occurs predominantly in young women. The median age at death for cases in NHANES III was 67.6 years (range, 49-91 years) and at diagnosis in the NHEFS was 68.9 years (range 61 to 81 years). No case was hypercalcemic. Thus, chance over-sampling of cancers known to be associated with hypercalcemia is unlikely to have influenced these findings.

Because the calcium measurements in the NHANES cohorts were obtained only once, there is a possibility of measurement error, which would tend to bias the results to the null. However, the serum concentration of ionized calcium is one of the most tightly controlled analytes in laboratory medicine. The group coefficient of variation (CV) for ionized calcium in the normal population is less than 3%.

Confounding was evaluated by several factors. There are numerous studies of dairy/calcium intake and ovarian cancer risk, the results of which are inconsistent. However, it is unlikely that these findings reflect confounding by dietary calcium intake because serum calcium levels in normal individuals are tightly controlled and are little influenced by dietary calcium intake. Height and BMI are modestly associated with ovarian cancer. However, the associations observed remained significant after adjustment for these factors. Other, established risk factors for ovarian cancer include BRCA status, nulliparity, and the non-use of oral contraceptives. NHANES did not contain data on BRCA status; potential confounding by this variable could not be evaluated. Total serum calcium levels are reported to be slightly higher in nulliparous women and to be slightly lower among users of oral contraceptives. Adjustment for parity and for oral contraceptive use did not materially influence the results. Several studies (but not all) suggest that serum levels of vitamin D may be inversely associated with risk of ovarian cancer. However, adjustment of the model for serum 25-OHD (data only available in NHANES III) caused only a 3-4% change in the association between serum calcium and ovarian cancer. Thus, the observations do not appear to be explicable by confounding by known risk factors for ovarian cancer.

A key question raised by these findings is whether higher levels of calcium in serum cause ovarian cancer or whether the higher calcium levels are a consequence of extant, subclinical ovarian cancer. Although the association between serum calcium and incident ovarian cancer observed in NHEFS might suggest a causal role for serum calcium, the minimum latent period for ovarian cancer, estimated to be 15-20 years, weakens this interpretation. Without being held to theory, it is possible that the positive associations between serum calcium and ovarian cancer reflects the influence of subclinical ovarian cancer on serum calcium levels, i.e., a paraneoplastic effect, similar to a phenomenon reported for prostate cancer.

In NHANES III, a greater relative hazard for increases in ionized serum calcium than for total serum calcium and for albumin-adjusted serum calcium (RH=2.44, 95% CI 1.45- 4.09, vs. RH=1.52, 95% CI 1.06-2.19 and RH =1.47, 95% C.I.=1.02-2.13) was observed. Without being held to theory, this observation may be related to the fact that many women with ovarian cancer have low serum albumin. The low serum albumin would lower the measured levels of total serum calcium, whereas the levels of ionized ("free") calcium would be unchanged. Although total serum calcium levels were adjusted for low serum albumin, albumin- adjusted serum calcium is known to be less sensitive than ionized serum calcium for detecting mild hypercalcemia.

Humoral hypercalcemia of malignancy (HHM) has been described in several types of ovarian cancer, predominantly small cell and clear cell carcinoma. The hypercalcemia in these cancers is caused by the production by the tumor of PTHrP which acts to resorb calcium from bone and inhibit calcium excretion by the kidney. Small cell carcinoma accounts for approximately 1% of ovarian cancers and is associated with HHM in approximately 66% of these cases. Clear cell carcinoma accounts for approximately 5% of ovarian cancers in the U.S. and is associated with HHM in 5-10% of these cases. Although small cell and clear cell carcinoma of the ovary are uncommon, PTHrP-mediated hypercalcemia also has been described in other types of ovarian cancer. Without being held to theory, it is hypothesized that there may be a spectrum of higher serum calcium in ovarian cancer in general, with small cell cancer and clear cell cancer inhabiting the far end of that spectrum. In addition to being a biomarker, serum calcium may participate in the pathophysiology of ovarian cancer. For example, the cell type classically believed to be responsible for ovarian cancer, ovarian surface epithelial cells, expresses functional calcium sensing receptors and proliferates in response to extracellular calcium.

In summary, in this biomarker discovery study, higher levels of calcium in serum were significantly positively associated with the risk of ovarian cancer in two prospective cohorts. The study has several strengths: it is prospective, uses population-based data from two nationally representative cohorts, and is the first to study ionized serum calcium. The existence of stored sera from sample sets of women with and without ovarian cancer should facilitate the confirmation or refutation of the association between serum calcium and ovarian cancer.

EXAMPLE 2

Study of Calcium Levels in Women with Adnexal Masses

Methods

Data were abstracted from the medical records of a consecutive series of 514 women with adnexal masses treated at the Wake Forest University Baptist Medical Center over approximately a five year period. The primary outcome was tumor pathology, which was unknown at the time that serum calcium and albumin and demographic data (menopausal status, age, etc.) was obtained from the medical records.

Information on the clinical and histopathological characteristics of the tumor was recorded. Benign and borderline histopathologies (including tumors of low malignant potential) were "controls". "Cases" were any malignant histopathology (excluding tumors of low malignant potential). The independent variables recorded included total serum calcium, serum albumin, age, body mass index, menopausal status, and parity. Age was centered around the mean. Serum calcium, serum albumin and body mass index were centered and scaled.

The sample was split into training and testing sets using a stratified random sampling approach to preserve the proportion of malignant cases. Using the training set, multivariable logistic generalized additive models were built with variables selected based on previous work. Continuous values were modeled as linear terms and non-linear terms, thin-plate regression splines with the degree of smoothness selected by generalized cross validation. Model fit was compared using the Akaike information criterion.

Using the testing data set, a risk prediction score was computed based on each of the selected logistic models. For each model, sensitivity, specificity, and positive and negative predictive values were computed at an optimum threshold (the maximum of the sum of sensitivity and specificity). Receiver operating characteristic (ROC) curves were constructed and the area under the ROC curve (AUC) was computed to evaluate the predictive power of the models.

All analyses were carried out in R using the 'caret' package for sampling, 'pROC' package for AUC analyses, and 'mgcv' for generalized additive models.

Results:

A total of 170 malignant tumors and 344 benign/borderline tumors were observed in the sample. From Table 4, in the training set, mean albumin-corrected calcium was 10.0 mg/dL for cases compared to 9.5 mg/dL for controls. Cases were more likely to have a lower body mass index, lower serum albumin, be menopausal, and have higher parity. Among ovarian cancer cases, 54% were stage 3C, and 74% were grade 3.

TABLE 4

Selected characteristics of women with ovarian malignancy (cases) and non-malignant ovarian tumors (controls) in the training dataset.

|  | Ovarian Cancer | Benign/Borderline |  |
| --- | --- | --- | --- |
| Number of participants | 86 | 171 |  |
| Age (years) | 62.7 (12.69) | 50.0 (15.55) | <0.01 |
| Body Mass Index (kg/m2) | 28.7 (8.35) | 32.2 (9.57) | <0.05 |
| Serum Creatinine (mg/dL) | 0.8 (0.25) | 0.8 (0.34) | 0.47 |
| Serum Calcium (mg/dL) | 9.3 (0.68) | 9.3 (0.48) | 0.68 |
| Albumin (g/dL) | 3.2 (0.73) | 3.8 (0.45) | <0.01 |
| Albumin-Corrected Calcium | 10.0 (0.44) | 9.5 (0.38) | <0.01 |
| Menopausal Status (%) | 0.8 (0.38) | 0.5 (0.50) | <0.01 |
| Parity (no. births) | 1.9 (1.84) | 1.8 (1.53) | <0.05 |

|  | Proportion in Category |
| --- | --- |
| Tumor Stage |  |
| 1 | 1% |
| 1A | 14% |
| 1C | 10% |
| 2 | 2% |
| 2A | 2% |
| 2B | 3% |
| 2C | 2% |
| 3 | 1% |
| 3A | 1% |
| 3B | 2% |
| 3C | 54% |
| 4 | 6% |
| None | 1% |
| Tumor Grade |  |
| 1 | 16% |
| 2 | 9% |
| 3 | 74% |
| None | 1% |

By itself, total serum calcium provided only a small predictive value (Table 5). However albumin-corrected serum calcium alone explained nearly 20% of the deviance in the outcome. This result underscores the importance of correcting total serum calcium for albumin Modeling calcium and albumin as separate variables, rather than correcting calcium for albumin provided additional information. The best fitting parsimonious model was one that incorporated serum calcium, serum albumin, age, and body mass index as non-linear terms, and also included menopausal status and parity.

TABLE 5

Deviance explained and Akaike Information Criteria for models built using training data

| Model | Deviance Explained | AIC |
| --- | --- | --- |
| Total Calcium | 0.2% | 341.9 |
| Albumin-Corrected Calcium | 19.9% | 275.1 |
| Calcium + Albumin | 25.6% | 258.0 |
| Calcium + Albumin as splines | 31.0% | 248.0 |
| Full Non-Linear Multivariable Model | 35.1% | 199.7 |
| +menopausal status + nulliparity | 34.3% | 189.7 |

*The full model includes calcium, albumin, age and body mass index as non-linear splines The characteristics of a randomly sampled testing set were very similar to the training set (Table 6). The predictive information provided by albumin-corrected calcium alone is appreciable. At an optimum threshold, the sensitivity is only 58%, but the specificity is 90%, yielding a positive predictive value (PPV) of 76% and a negative predictive value of 79% in the sample, with an AUC of 0.77.

TABLE 6

Selected characteristics of women with ovarian cancer benign or borderline adnexal masses in the testing dataset.

|  | Ovarian Cancer | Benign/Borderline | P-value |
| --- | --- | --- | --- |
| Number of participants | 84 | 173 |  |
| Age (years) | 60.8 (14.79) | 53.9 (14.56) | <0.01 |
| Body Mass Index (kg/m2) | 28.3 (9.66) | 29.6 (8.54) | 0.32 |
| Serum Creatinine (mg/dL) | 0.8 (0.23) | 0.8 (0.25) | 0.77 |
| Serum Calcium (mg/dL) | 9.3 (0.53) | 9.4 (0.46) | 0.64 |
| Albumin (g/dL) | 3.3 (0.73) | 3.9 (0.43) | <0.01 |
| Albumin-Corrected Calcium | 9.9 (0.43) | 9.5 (0.41) | <0.01 |
| Menopausal Status (%) | 0.8 (0.40) | 0.6 (0.49) | <0.01 |
| Parity (no. births) | 1.8 (1.40) | 1.8 (1.32) | <0.05 |

|  | Proportion in Category |
| --- | --- |
| Tumor Stage |  |
| 1 | 1% |
| 1A | 17% |
| 1C | 8% |
| 2 | 2% |
| 2A | 2% |
| 2B | 1% |
| 2C | 1% |
| 3 | 1% |
| 3A | 0% |
| 3B | 1% |
| 3C | 50% |
| 4 | 7% |
| Tumor Grade |  |
| 1 | 11% |
| 2 | 10% |
| 3 | 74% |
| None | 6% |

The best fit model, the OVERA™ prediction model, that includes non-linear terms achieved an AUC of 0.83 with a sensitivity of 72% and specificity of 83%, a PPV of 71% and a NPV of 85%. (Table 7) The p-value comparing the OVERA™ model to a prediction model using albumin-corrected calcium alone is p<0.001. The OVERA™ prediction model is a multivariable generalized additive model that incorporates serum calcium, serum albumin, and the age and body mass index of the patient as inputs. While the model produces a continuous value of outputs, in general the values are scaled as a range of numbers such as a prediction score ranging from 1 to 10 as an output, where 1 represents the lowest risk and 10 represents the highest risk of ovarian cancer. The output prediction score is a non-linear combination of the inputs using thin plate-regression splines with the degree of smoothness determined by generalized cross-validation. The test is positive when the prediction score exceeds the threshold established by the value that optimizes the sensitivity and specificity of the test. For example, in the initial study, a scaled predicted score for the OVERA™ test of 2.7 maximizes the sum of sensitivity and specificity and a value over 2.7 would indicate a positive test. In addition, there is a confidence interval around each score to account for sampling variability.

TABLE 7

Predictive performance of Overa ™ models in discriminating ovarian cancer from benign or borderline adnexal masses in the testing dataset.

| Model | AUC | Sensitivity | Specificity | PPV | NPV |
|---|---|---|---|---|---|
| Total Calcium | 0.49 | 34% | 71% | 41% | 66% |
| Albumin-Corrected Calcium | 0.77 | 58% | 90% | 76% | 79% |
| Calcium + Albumin | 0.82 | 70% | 83% | 70% | 83% |
| Calcium + Albumin as splines | 0.82 | 72% | 81% | 68% | 84% |
| Full Non-Linear Multivariable Model | 0.83 | 72% | 83% | 71% | 85% |

The non-linear multivariable model includes calcium, albumin, age, and body mass index as splines Due to the simplicity and routine nature of the measurement of total calcium and albumin in plasma, the OVERA™ test described herein provides a significant advantage over the only approved ovarian cancer detection test, OVA1™. The OVA1 test combines the results of five immunoassays into a proprietary algorithm to produce a numerical score indicative of the likelihood of malignancy. The test described herein is more sensitive in detecting a risk of ovarian cancer in pre-menopausal women than in post-menopausal women (where it is also quite sensitive). This is important because the OVA1 test is not particularly good at detecting risk in premenopausal women and thus this would be an advantage of the test described herein.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A preoperative method of determining a greater likelihood that an adnexal mass in a female subject is malignant or benign, comprising
providing a blood sample collected from the subject;
isolating serum or plasma from the blood sample to obtain a serum or plasma sample;
determining a total calcium level and an albumin level in the serum or plasma sample;
comparing the total calcium level and the albumin level of the serum or plasma sample to a multivariable generalized additive predictive model that includes total serum or plasma calcium and albumin for a population including patients with malignant ovarian masses and patients with benign ovarian masses, and the age and body mass of the population as covariates, wherein a model output is scaled as a range; and providing a predictive score for the female subject based upon the comparison; and
determining that the adnexal mass in the female subject is likely to be malignant or likely to be benign based on the predictive score for the female subject.

2. The method of claim 1, wherein it is determined that the adnexal mass is likely to be malignant and further comprising referring the subject to a gynecological surgeon for removal of the malignant adnexal mass.

3. A preoperative method of determining if an adnexal mass in a female subject is likely to be malignant or likely to be benign, comprising
providing a blood sample collected from the subject;
isolating serum or plasma from the blood sample to obtain a serum or plasma sample;
determining a total calcium level and an albumin level in the serum or plasma sample, and calculating an albumin corrected calcium level of the serum or plasma sample from the subject;
comparing the albumin-corrected calcium level of the serum or plasma sample from the subject to a predictive model that includes albumin-corrected calcium levels for a normal distribution of a population not characterized as at risk for ovarian cancer; and
determining that the adnexal mass is malignant when the albumin-corrected calcium level in the serum or plasma sample is high normocalcemic to hypercalcemic or deviates upward from normal based on the predictive model, determining that the adnexal mass is benign when the albumin-corrected calcium level in the serum or plasma sample is normocalcemic or lower, is normal based on the predictive model or deviates downward from normal based on the predictive model, wherein the albumin-corrected calcium level in the serum or plasma sample is calculated as (0.8 times the difference between 4.0 g/dL and the albumin level in the serum or plasma sample)+ (the total calcium level in the serum or plasma sample in mg/dL).

4. The method of claim 3, wherein it is determined that the adnexal mass is likely to be malignant and further comprising referring the subject to a specialist for removal of the malignant adnexal mass.

5. The method of claim 3, wherein the predictive model further comprises a covariate and the covariate is age, body mass index, menopausal status, parity, or a combination thereof.

6. The method of claim 3, wherein the albumin-corrected calcium level that deviates upward from normal is greater than or equal to 9.8 mg/dl.

7. A method of screening for an increased risk of ovarian cancer in a human female subject, comprising
providing a blood sample collected from the subject;
isolating serum or plasma from the blood sample to obtain a serum or plasma sample;
determining a level of total or ionized calcium in the serum or plasma sample;
comparing the level of total or ionized calcium in the serum or plasma sample to a normal distribution from a population not characterized as at risk of ovarian cancer, wherein the normal distribution is adjusted using age as a covariate, and
determining that the subject has an increased risk of ovarian cancer when the level of total or ionized calcium in the serum or plasma sample is in an upper tertile compared to the age-adjusted normal distribution,
wherein the subject is experiencing one or more symptoms of ovarian cancer and/or wherein the subject has a family history of breast or ovarian cancer.

8. The method of claim 7, wherein an increase in total or ionized serum calcium is not accompanied by an increase in serum parathyroid hormone, or is accompanied by a detectable level of parathyroid-hormone-related peptide.

9. The method of claim 7, wherein the level of total or ionized calcium in the serum or plasma sample in an upper tertile compared to the normal distribution is increased 0.25 mg/dl or more compared to a midpoint of the normal distribution.

10. The method of claim 7, wherein when said serum or plasma sample is in the upper tertile compared to the normal distribution further detecting CA-125 in a blood sample from the subject, screening with ultrasound, or both.

11. The method of claim 7, wherein when said serum or plasma sample is in the upper tertile compared to the normal distribution further detecting beta-2 microglobulin, CA 125-II, apolipoprotein Al, prealbumin, and transferrin in a blood sample from the subject.

12. The method of claim 7, wherein the subject is experiencing one or more symptoms of ovarian cancer and/or has a family history of breast or ovarian cancer and has been tested for beta-2 microglobulin, CA 125-II, apolipoprotein Al, prealbumin, and transferrin in a blood sample from the subject.

13. The method of claim 7, wherein when the subject is found to be at risk of ovarian cancer, the method further comprises assaying a blood sample for human epididymis protein 4.

14. A method of screening for an increased risk of ovarian cancer in a human female subject, comprising
providing a first blood sample collected from the subject at a first time and a second blood sample collected from the subject at a second time;
isolating serum or plasma from the first blood sample and the second blood sample to obtain a first serum or plasma sample and a second serum or plasma sample;
determining a level of total or ionized calcium in the first and second serum or plasma samples; and
determining that the subject has an increased risk of ovarian cancer when the level of total or ionized calcium in the second serum or plasma sample is increased compared to the first serum or plasma sample, wherein increased total or ionized calcium in the second serum or plasma sample is increased by 10% or more, and the increase in total or ionized calcium is not accompanied by an increase in parathyroid hormone, and/or is accompanied by a detectable level of parathyroid-hormone related peptide,
wherein the subject is experiencing one or more symptoms of ovarian cancer and/or wherein the subject has a family history of breast or ovarian cancer.

15. The method of claim 14, wherein a time interval from the first time to the second time is 6 weeks.

16. The method of claim 14, wherein the subject has been tested for beta-2 microglobulin, CA 125-II, apolipoprotein Al, prealbumin, and transferrin in a blood sample from the subject.

* * * * *